US006855312B1

(12) United States Patent
Craig et al.

(10) Patent No.: US 6,855,312 B1
(45) Date of Patent: Feb. 15, 2005

(54) HAIR CARE COMPOSITION

(75) Inventors: Ailsa Helen Louise Craig, Nottinghamshire (GB); Edward Galley, Nottinghamshire (GB); Stewart Paul Long, Nottinghamshire (GB); Melanie Ann Pykett, Nottinghamshire (GB)

(73) Assignee: The Boots Company PLC, Nottingham (GB)

( * ) Notice: Subject to any disclaimer, the term of this patent is extended or adjusted under 35 U.S.C. 154(b) by 0 days.

(21) Appl. No.: 10/030,147

(22) PCT Filed: Jul. 26, 2000

(86) PCT No.: PCT/EP00/07196

§ 371 (c)(1),
(2), (4) Date: May 20, 2002

(87) PCT Pub. No.: WO01/06997

PCT Pub. Date: Feb. 1, 2001

(30) Foreign Application Priority Data

Jul. 28, 1999 (GB) .............................. 9917729

(51) Int. Cl.$^7$ ................................ A61K 7/075
(52) U.S. Cl. .................... 424/74; 426/701; 426/728; 514/474
(58) Field of Search .................. 424/74, 728, 701, 424/901, 776; 514/474

(56) References Cited

U.S. PATENT DOCUMENTS 5,102,659 A   4/1992  Hudson 5,962,517 A   10/1999  Murad
6,066,327 A   5/2000   Gubernick et al.

FOREIGN PATENT DOCUMENTS

DE   42 27 806     2/1993
DE   2746008       9/1997
WO   WO 98/42309   10/1998

OTHER PUBLICATIONS

DE Abstract 4419783(12/95).*
RU abstract 2061463(6/93).*
JP abstract 07291838(11/95).*

* cited by examiner

Primary Examiner—Jyothsna Venkat
(74) Attorney, Agent, or Firm—Rothwell, Figg, Ernst & Manbeck, P.C.

(57) ABSTRACT

Hair care compositions containing a synergistic mixture of three anti-free-radical agents selected from (a) ascorbic acid, its salts and esters; (b) tocopherol and its esters, such as tocopherol acetate; and (c) herbal extracts selected from morus alba, origanum vulgare, panax ginseng, rosmarinus officinalis, camellia sinensis and grape seed extract in a suitable diluent or carrier. Preferred synergistic mixtures are Origanum vulgare, sodium ascorbyl phosphate and morus alba. Origanum vulgare, sodium ascorbyl phosphate and panax ginseng. Panax ginseng, morus alba and Origanum vulgare. Sodium ascorbyl phosphate, morus alba and camellia sinensis. Sodium ascorbyl phosphate, morus alba and grape seed Origanum vulgare, panax ginseng and rosmarinus officinalis.

17 Claims, No Drawings

HAIR CARE COMPOSITION

This application is the U.S. national stage entry of International Application No. PCT/EP00/07196, filed Jul. 28, 2000, which claims priority to British Application No. 9917729.7, filed Jul. 28, 1999, and incorporates these applications by reference in their entirety.

The present invention relates to hair care compositions having protecting and conditioning properties and to methods of using such compositions to treat hair.

The hair is exposed to a number of environmental challenges. Such exposure can generate free-radicals, especially on exposure to sunlight and/or heat, and presence of high concentrations of free radicals is generally seen as undesirable in a toiletries composition to be used on the hair. Free radicals, which are generated by factors such as UV radiation (present in sunlight), heat and/or by chemical reaction, are implicated in the process of damage to hair, reduction in shine, poor feel, and fading of hair colour.

There are a number of haircare compositions, commercially available, which seek to minimise the damage to the hair by the inclusion of certain agents. In particular materials such as vitamins and herbal extracts have widely been known to reduce the formation of free-radicals. However to achieve good efficiency high levels of these materials have to be used and this can result in dark aesthetically unpleasing products that can stain the hair The hair care compositions of the present invention have been shown to protect the hair more effectively from free radicals and are cosmetically and aesthetically more suitable than known hair care compositions. Therefore the hair care compositions of the present invention may be used to provide improved protection against damage to hair caused by exposure to factors such as sunlight, environmental and/or atmospheric pollution, heat from styling the hair and/or chemical treatment of the hair (for example curling, perming, straightening, dyeing and/or bleaching). The hair care compositions of the present invention may comprise conventional hair care products and/or specific hair protection products which may be used for example as protective pre-treatments prior to heat or chemical treatment of the hair.

The term "hair care composition" as used herein includes so-called "hot oil" treatments, shampoos, conditioners, hair dyes, mousses, foams, gels, creams, waxes, masks, muds, semi-solid structured styling pastes (also known as putties), styling sprays, lotions and rinses, all suitable for use on the hair of animals, preferably on human hair, most preferably hair on the human head.

Therefore broadly according to the present invention there is provided a hair care composition containing a combination of anti-free-radical ingredients that when combined together give a synergistic improvement in activity allowing improved protection and condition to be provided for the hair without the drawback of aesthetically unpleasant product appearance and the chance of hair staining.

The present invention provides hair care compositions containing a synergistic mixture of three anti free radical agents selected from (a) ascorbic acid, its salts and esters, particularly sodium ascorbyl phosphate, magnesium ascorbyl phosphate and ascorbyl palmitate (b) tocopherol and its esters, such as tocopherol acetate and (c) herbal extracts, particularly *morus alba*, such as that available under the trade name "Mulberry Concentrate" from Aston Chemicals; *origanum vulgare*, such as that available under the trade name "Pronalen Origanum HSC" from S Black Ltd; *panax ginseng*, such as that available under the trade name "Ginseng 1.1 extract 4294" from S Black Ltd; *rosmarinus officinalis*, such as that available under the trade name Herbal Rosemary WS from Chesham Chemicals or Pronelen Rosemary extract from S.Black Ltd]; camellia sinensis such as that available under the trade name "Herbal Extract Green Tea 75% Solids" from Nichimen Europe; and grape seed extract such as that available under the trade name Grape Seed Extract WS from S.Black Ltd. In combination with a suitable diluent or carrier. The agents used in the present invention are already known for their individual ability to quench free radicals and prevent oxidative damage to the hair. However the present invention discloses that certain combinations of these agents have an efficacy much greater than expected. This has been demonstrated experimentally.

The commercially available sources of the anti free-radical agents used in the present invention consist of the anti free-radical agents but these may also comprise diluents and/or carriers. Thus there may be some confusion as to the actual level of agent within a commercially available product. Accordingly, the amounts of anti free-radical agents used in the present invention are expressed as dry weights, as understood by a man skilled in the art.

The total amount of anti-free radical agents present in the composition may range from 0.003% to 10% by weight. Where the synergistic mixture of anti free-radical agents is comprised solely of herbal extracts, then a preferred total amount of anti free-radical agents is 0.005% to 1%w/w, most preferably 0.01% to 0.6% by weight of the composition.

Preferably, the individual anti-free-radical agents that comprise the synergistic mixtures may be present in an amount of from about 0.001% to about 10% by weight, more preferably from about 0.003% to about 5% by weight, most preferably 0.004 to 0.2% by weight of the composition.

Particularly preferred synergistic combinations of anti free-radical agents suitable for inclusion in a hair care composition are:

*Origanum vulgare*, sodium ascorbyl phosphate and *morus alba*.

*Origanum vulgare*, sodium ascorbyl phosphate and *panax ginseng*.

*Panax ginseng*, *morus alba* and *origanum vulgare*.

Sodium ascorbyl phosphate, *morus alba* and *camellia sinensis*.

Sodium ascorbyl phosphate, *morus alba* and grape seed.

*Origanum vulgare, panax ginseng* and *rosmarinus officinalis*.

A hair care composition containing a synergistic combination of anti free-radical agents has a multitude of advantages. Such anti free-radical agents are usually highly coloured. If they are used individually in amounts necessary to be totally effective, it, is likely that the hair care composition would stain both skin and clothes and would dye the hair. Further, even at lower levels the agents give the composition a cosmetically unacceptable appearance. Thus most conventional hair compositions use less of an anti free-radical agent than necessary to provide total protection. With the present invention because of the increased efficacy of the synergistic mixture of anti-free radical agents it is possible to include the anti free-radical agents in sufficient amounts to provide an effective defence against the action of free radicals. Thus use of the composition will give the users hair improved shine, feel, manageability, flexibility, colour and will help protect the hair from damage. All this is provided without the aforementioned disadvantages of staining, dyeing and unacceptable cosmetic appearance.

Alternatively, if the same level of protection as a conventional formulation is required, then the increased efficacy of the synergistic mixture of anti free-radical agents means that the composition will require much lower quantities of the anti free-radical agents than a conventional formulation. Not only are any problems with highly coloured formulations reduced (staining, dyeing, cosmetic appearance), but the cost of the formulation is likely to be cheaper as well.

To further reduce the generation of free-radicals by the UV radiation in sunlight, compositions of the present invention may further comprise any acceptable sunscreening agent (that is an agent which acts to absorb and/or reflect UV radiation present in sunlight) and which would be acceptable for use in a hair-care composition (for example suitable for use on the human head). Such sunscreening agents may comprise inorganic sunscreens (for example zinc oxide and/or titanium dioxide preferably of microfine (<100 nm) particle size) and/or organic sunscreens (for example p-aminobenzoic acids, esters and derivatives, methoxycinnamate esters, benzophenones [such as benzophenone-4 {available commercially under the trade name Uvinul MS40}]; dibenzoylmethanes and/or salicylate esters). The sunscreening agents may be present in an amount of from about 0.1% to about 10% by weight of the composition.

Further components may be added to the hair care composition as is well-known to those skilled in the art.

For example, preservatives may be added to the composition such as 2-bromo-2-nitropropane-1,3-diol (bronopol), which is available commercially under the trade name Myacide RTM), benzyl alcohol, diazolidinyl urea, imidazolidinyl urea, methyl paraben, phenoxy ethanol, propyl paraben, sodium methyl paraben and sodium propyl paraben, suitably in an amount of from about 0.01% to about 10% by weight of the composition.

Thickeners and viscosity modifying agents may be added to the composition, such as amine oxides, block polymers of ethylene oxide and propylene oxide (for example, those available from BASF Wyandotte under the trade name "Pluronic" RTM), ethoxylated fatty alcohols, cellulosic derivatives such as hydroxypropylmethyl cellulose, salt (NaCl), phthalic acid amide, polyvinyl alcohols and fatty alcohols, suitably in an amount of from about 0.5% to about 10% by weight of the composition.

Sequestering agents may be added to the composition, such as ethylenediamine tetraacetic acid and salts thereof, suitably in an amount of from about 0.005% to about 0.5% by weight of the composition.

The composition may also include resins such as: octylacrylamide/acrylates/butylaminomethacrylate copolymer (available under the trade name Amphomer RTM); ethyl ester of polyvinylmethyl (hereinafter known as PVM)/methylacrylate (hereinafter known as MA) copolymer (available under the trade name Ultrahold 8A RTM); vinyl acetate (hereinafter known as VA)/crotonates/vinyl neodecanate copolymer (available under the trade name Adhesive 28-2930 NAL); acrylates/acrylamide copolymer (available under the trade name Gantrez ES225 RTM); vinyl acetate/crotonic acid/vinyl propionate copolymer (available under the trade name Luviset CAP RTM); polyvinylpropionate (hereinafter known as PVP)/VA/vinylpropionate copolymer (available under the trade name Laviskol VAP RTM); octylacrylamide/acrylate copolymer (available under the trade names Versatyl 90 RTM or Lovocryl 47 RTM); vinyl caprolactam/PVP/dimethylaminoethyl methacrylate copolymer (available under the trade name ($H_2O$ LD EP-1); PVM/MA copolymer (available under the trade name Gantrez RTM); and vinyl acetate/butyl maleate/isobornyl acrylate copolymer (available under the trade name Advantage CP RTM), These resins may be present suitably in an amount of from about 0.1% to about 10% by weight of the composition.

The composition, may also include slip aids such as phenyl trimethicone, suitably in an amount of from about 0.1% to about 10% by weight of the composition.

The composition may also include vitamins such as biotin, suitably in an amount of from about 0.01% to about 1.0% by weight of the composition.

The composition may also include waxes such as cocoa butter suitably in an amount of from about 1% to about 99% by weight of the composition.

The composition may also include gelling agents such as PVM, MA, or a decadiene crosspolymer (available under the trade name Stabilez 06), suitably in an amount of from about 0.1% to about 2% by weight of the composition.

The composition may also comprise suitable, cosmetically acceptable diluents, carriers and/or propellants such as dimethyl ether.

The composition may also include pearlising agents such as stearic monoethanolamide, suitably in an amount of from about 0.01% to about 10% by weight of the composition.

Perfumes may be added suitably in an amount of from about 0.01% to about 2% by weight of the composition, as may water soluble dyes such as tartrazine, suitably in an amount of from about a trace amount (such as $1\times10^{-5}\%$) to about 0.1% by weight of the composition.

The composition may also include pH adjusting agents such as sodium hydroxide, aminomethyl propanol, triethanolamine, suitably in an amount of from about 0.01% to about 10% by weight of the composition.

The composition may be buffered by means well known in the art, for example by use of buffer systems comprising succinic acid, citric acid, lactic acid, and acceptable slits thereof, phosphoric acid, mono- or disodium phosphate and sodium carbonate. Suitably, the composition may have a pH between about 3 and about 10, preferably between about 4 and about 8.

The composition may also include an antidandruff agent such as salicylic acid or zinc pyrithione or octopyrox suitably in an amount of from about 0.1% to about 5% by weight of the composition.

Surfactants may be included, such as cosmetically acceptable salts of alkyl ether sulphates, alkyl and alkylamidoalkyl betaines, ethoxylated alcohols, polyethyleneglycol carboxylates, acceptable salts of alkyl sulphates (such as ammonium lauryl sulphate), acceptable salts of alkyl ether sulphates (such as ammonium laureth sulphate or sodium laureth sulphate), sulphosuccinates (such as disodium laureth sulphosuccinate), amphoacetates and amphodiacetates (such as disodium cocoamphodiacetate), alkylpolyglucosides and alcohol sulphonates.

In accordance with a further aspect of the present invention there is provided a method of treating hair (for example washing, conditioning and/or styling hair) by application to the hair of a composition as described herein.

The invention will be illustrated with reference to the non-limiting tests and formulation examples described hereinafter:

EXAMPLE 1

Hair Conditioner

| Ingredients | % W/W |
| --- | --- |
| Aqua | to 100 |
| Cetyl alcohol | 3 |
| Cetrimonium chloride | 0.759 |

-continued

| Ingredients | % W/W |
| --- | --- |
| Hydroxyethylcellulose | 0.6 |
| Propylene glycol | 0.493 |
| Panthenol | 0.375 |
| Parfum | 0.3 |
| Benzophenone-4 | 0.2 |
| Sodium chloride | 0.15 |
| Wheat amino acids | 0.14 |
| Amodimethicone | 0.105 |
| Alcohol denat. | 0.095 |
| Dimethicone propyl PG-betaine | 0.09 |
| Citric acid | 0.026 |
| Tetrasodium EDTA | 0.02 |
| Trideceth-10 | 0.0045 |
| *Origanum vulgare* | 0.009 |
| *Panax ginseng* | 0.006 |
| *Morus alba* | 0.0046 |

The EDTA and hydroxyethylcellulose were added to the water and mixed using a homogeniser to hydrate the polymer. Citric acid, benzophenone and cetrimonium chloride were added. This was then heated to 70° C.

Cetyl alcohol was heated to 70° C. in a separate vessel and was then added to the aqeuous mixture using a homogeniser. The mixture was then cooled to below 40° C. using a propeller stirrer. The remaining materials including the antioxidant complex were then added and the product was made to weight with purified water.

EXAMPLE 2

Intensive Conditioner

| Ingredients | % W/W |
| --- | --- |
| Aqua | to 100 |
| Cetearyl alcohol | 4.6 |
| Arachidyl propionate | 2 |
| Dimethicone | 2 |
| Panthenol | 1.5 |
| Stearamidopropyl dimethylamine | 1.5 |
| Hydroxyethylcellulose | 0.75 |
| Amodimethicone | 0.7 |
| Citric acid | 0.503 |
| Cetrimonium chloride | 0.435 |
| PEG-20 stearate | 0.4 |
| Parfum | 0.3 |
| Propylene glycol | 0.29 |
| Benzophenone-4 | 0.2 |
| Sodium chloride | 0.15 |
| Wheat amino acids | 0.14 |
| Polyquaternium-39 | 0.1 |
| Alcohol denat. | 0.095 |
| Trideceth-10 | 0.03 |
| BHT | 0.025 |
| Isopropyl alcohol | 0.02 |
| Tetrasodium EDTA | 0.02 |
| *Origanum vulgare* | 0.009 |
| *Panax ginseng* | 0.006 |
| *Morus alba* | 0.0046 |

The EDTA and hydroxyethylcellulose were added to the water and mixed using a homogeniser to hydrate the polymer. The citric acid and cetrimonium chloride were added and mixed using a propeller stirrer. The mixture was then heated to 70° C. In a separate vessel, the waxes, dimethicone and BHT were mixed and heated to 70° C. until melted and uniform. This mixture was then was added to the aqueous mixture and this was mixed until uniform. The resulting mixture was then cooled to below 40° C. with stirring and the remaining materials including the antioxidant complex were then added and the product was made to weight using purified water.

EXAMPLE 3

Leave in Conditioner

| Ingredients | % W/W |
| --- | --- |
| Aqua | to 100 |
| PEG-40 hydrogenated castor oil | 2 |
| Dipropylene glycol | 1 |
| Phenoxyethanol | 0.85 |
| Parfum | 0.4 |
| Panthenol | 0.375 |
| Propylene glycol | 0.29 |
| Methylparaben | 0.2 |
| Benzophenone-4 | 0.2 |
| Alcohol denat. | 0.095 |
| Polyquaternium-10 | 0.091 |
| Sodium chloride | 0.3 |
| Wheat amino acids | 0.028 |
| Sodium hydroxide | 0.026 |
| *Origanum vulgare* | 0.009 |
| *Panax ginseng* | 0.006 |
| *Morus alba* | 0.0046 |

The polyquaternium-10 was added to the water and hydrated using a propeller stirrer. The methylparaben was pre-dispersed in the dipropylene glycol, gently heated to melt and then added to the hydrated polyquaternium-10 mixture. The remaining materials including the antioxidant complex were then added and the product was mixed and made to weight with purified water.

EXAMPLE 4

Gentle Shampoo

| Ingredients | % W/W |
| --- | --- |
| Aqua | to 100 |
| Sodium laureth sulfate | 8.25 |
| Cocamidopropyl betaine | 2.8 |
| Sodium chloride | 1.794 |
| Cocamide DEA | 1.63 |
| PEG-6 cocamide | 1 |
| Parfum | 0.5 |
| Panthenol | 0.375 |
| Propylene glycol | 0.29 |
| Benzophenone-4 | 0.2 |
| Glycerin | 0.2 |
| Phenoxyethanol | 0.162 |
| Wheat amino acids | 0.14 |
| Alcohol denat. | 0.095 |
| Citric acid | 0.05 |
| Methyldibromo glutaronitrile | 0.04 |
| Tetrasodium EDTA | 0.02 |
| *Origanum vulgare* | 0.009 |
| *Panax ginseng* | 0.006 |
| *Morus alba* | 0.0046 |

EDTA, sodium chloride, citric acid and benzophenone-4 were added to the water. This was followed by the addition of sodium laureth sulfate, methyldibromo glutaronitrile, wheat amino acids and the antioxidant complex. PEG-6 cocamide and cocamide DEA were heated gently until liquified. The parfum was added and mixed. This was then added to the above mixture. The cocamidopropyl betaine and remaining materials were then added and mixed. The product was made to weight using purified water.

EXAMPLE 5

Anti-Dandruff Shampoo

| Ingredients | % W/W |
|---|---|
| Aqua | to 100 |
| Sodium laureth sulfate | 5.9 |
| Disodium laureth sulfosuccinate | 4 |
| Laureth-3 | 3 |
| Cocamidopropyl betaine | 2.45 |
| Sodium chloride | 1.926 |
| Dipropylene glycol | 1 |
| Parfum | 0.5 |
| Piroctone olamine | 0.5 |
| Panthenol | 0.375 |
| Propylene glycol | 0.29 |
| Disodium phosphate | 0.25 |
| Benzophenone-4 | 0.2 |
| Wheat amino acids | 0.14 |
| Alcohol denat. | 0.095 |
| Citric acid | 0.063 |
| Tetrasodium EDTA | 0.02 |
| Preservative | 0.2 |
| *Origanum vulgare* | 0.009 |
| *Panax ginseng* | 0.006 |
| *Morus alba* | 0.0046 |

EDTA, citric acid and benzophenone-4 were mixed into the water. Sodium laureth sulfate, disodium laureth sulfosuccinate, dipropylene glycol, disodium phosphate, wheat amino acids and the antioxidant complex were added and the product was stirred until uniform. The piroctone olamine was dispersed in the parfum and added to the laureth-3. This mixture was added to the bulk and stirred. The remaining materials were then added and the product was made to weight with purified water.

EXAMPLE 6

Anti-Chlorine Shampoo

| Ingredients | % W/W |
|---|---|
| Aqua | to 100 |
| Sodium laureth sulfate | 7.6 |
| Cocamidopropyl betaine | 2.8 |
| Sodium chloride | 1.694 |
| Laureth-3 | 1 |
| Phenoxyethanol | 0.852 |
| Parfum | 0.5 |
| Disodium phosphate | 0.4 |
| Panthenol | 0.375 |
| Propylene glycol | 0.29 |
| Methylparaben | 0.2 |
| Benzophenone-4 | 0.2 |
| Wheat amino acids | 0.14 |
| Propylparaben | 0.1 |
| Sodium thiosulfate | 0.1 |
| Alcohol denat. | 0.095 |
| Sodium hydroxide | 0.06 |
| Sodium phosphate | 0.06 |
| Tetrasodium EDTA | 0.02 |
| *Origanum vulgare* | 0.009 |
| *Panax ginseng* | 0.006 |
| *Morus alba* | 0.0046 |

Benzophenone, sodium chloride, sodium phosphate, disodium phosphate and EDTA were added to the water and mixed. Sodium laureth sulfate, phenoxyethanol, panthenol, wheat amino acids and the antioxidant complex were then added and stirred. The preservatives were pre-mixed in the laureth-3 and heated slightly to melt the powders. This was added to the product. The remaining materials were added and the product was made to weight using purified water.

EXAMPLE 7

Hair Gel

| Ingredients | % W/W |
|---|---|
| Aqua | to 100 |
| Cyclomethicone | 6.6 |
| Dimethiconol | 0.9 |
| Phenoxyethanol | 0.8 |
| Propylene glycol | 0.79 |
| Panthenol | 0.75 |
| Carbomer | 0.7 |
| Aminomethyl propanol | 0.4 |
| Benzophenone-4 | 0.2 |
| Parfum | 0.2 |
| Alcohol denat. | 0.095 |
| Tetrasodium EDTA | 0.05 |
| Sodium chloride | 0.03 |
| Wheat amino acids | 0.028 |
| *Origanum vulgare* | 0.009 |
| *Panax ginseng* | 0.006 |
| *Morus alba* | 0.0046 |

EDTA and benzophenone-4 were added to the water using an homogeniser. The carbomer was added and hydrated with continued homogenising. The phenoxyethanol, cyclomethicone, dimethiconol, propylene glycol and panthenol were then added and mixed until homogenous. The remaining materials including the antioxidant complex were added and the bulk was homogenised until uniform and the product was made to weight using purified water.

EXAMPLE 8

Semi-solid Structured Styling Paste for Hair

This type of product is also known as a hair putty

| Ingredients | % W/W |
|---|---|
| Aqua | to 100 |
| Cetearyl alcohol | 10.9 |
| Lanolin | 7 |
| PVP | 6 |
| Paraffin | 6 |
| PVP/VA copolymer | 5.7 |
| Carnauba | 3 |
| Petrolatum | 2 |
| Polyquaternium-11 | 2 |
| PEG-20 stearate | 1.9 |
| Paraffinum liquidum | 1 |
| Propylene glycol | 0.8 |
| Phenoxyethanol | 0.6 |
| Dimethicone | 0.5 |
| Panthenol | 0.375 |
| Cetrimonium chloride | 0.35 |
| Dimethicone propyl PG-betaine | 0.225 |
| Benzophenone-4 | 0.2 |
| Methylparaben | 0.12 |
| Alcohol denat. | 0.095 |
| *Origanum vulgare* | 0.009 |
| *Panax ginseng* | 0.006 |
| *Morus alba* | 0.0046 |

The PVP/VA copolymer, PVP and benzophenone-4 were added to the water and stirred until homogenous. This was then heated to 70° C. In a separate vessel, the waxes were mixed and heated to 70° C. until all materials had melted. The hot waxes were then added to the aqueous mixture and mixed using a propeller stirrer until homogenous. The mixture was then cooled to below 60° C. and the remaining materials, including the antioxidant complex were then added and the product was stirred until uniform. The product was made to weight using purified water.

EXAMPLE 9

Moisturising Conditioner

| Ingredients | % W/W |
| --- | --- |
| Aqua | to 100 |
| Cetyl alcohol | 4 |
| Dimethicone | 2 |
| Hydroxyethylcellulose | 0.8 |
| Cetrimonium chloride | 0.765 |
| Panthenol | 0.75 |
| Propylene glycol | 0.64 |
| Parfum | 0.3 |
| Benzophenone-4 | 0.2 |
| Amodimethicone | 0.175 |
| Dimethicone propyl PG-betaine | 0.15 |
| Sodium chloride | 0.15 |
| Wheat amino acids | 0.14 |
| Alcohol denat. | 0.095 |
| Citric acid | 0.026 |
| Tetrasodium EDTA | 0.02 |
| Trideceth-10 | 0.009 |
| *Origanum vulgare* | 0.009 |
| *Panax ginseng* | 0.006 |
| *Morus alba* | 0.0046 |

EDTA and hydroxyethylcellulose were added to the water using homogenising to hydrate the polymer. The benzophenone-4 and Laureth-3 were then added and the bulk was heated to 70° C. In a separate vessel, the cetyl alcohol was heated to 70° C. until melted and was then added to the bulk and mixed with a homogeniser until uniform. The product was cooled and the remaining materials, including the antioxidant complex were then added and mixed. The product was made to weight using purified water.

EXAMPLE 10

Spray Gel

| Ingredients | % W/W |
| --- | --- |
| Phase 1 | |
| Aqua | to 100 |
| PVP/VA copolymer | 4.9 |
| Isopropyl alcohol | 2.5 |
| Propylene glycol | 2.29 |
| Glycerin | 2 |
| Panthenol | 0.375 |
| Benzophenone-4 | 0.2 |
| Sodium chloride | 0.03 |
| Wheat amino acids | 0.028 |
| *Origanum vulgare* | 0.009 |
| *Panax ginseng* | 0.006 |
| *Morus alba* | 0.0046 |
| Phase 2 | |
| PEG-40 hydrogenated castor oil | 1 |
| Parfum | 0.3 |
| Phase 3 | |
| Alcohol denat. | 45 |
| Dimethicone copolyol | 1 |

The materials in phase 1 were mixed until uniform using a propeller stirrer. The materials in phase 2 were pre-mixed and added to phase 1. The materials in phase 3 were mixed and added to the bulk. The product was made to weight using purified water.

EXAMPLE 11

Dry Scalp Shampoo

| Ingredients | % W/W |
| --- | --- |
| Aqua | to 100 |
| Sodium laureth sulfate | 7 |
| Sodium chloride | 2.23 |
| Cocamidopropyl betaine | 1.96 |
| Laureth-3 | 1 |
| Panthenol | 0.375 |
| Propylene glycol | 0.29 |
| Piroctone olamine | 0.25 |
| Benzophenone-4 | 0.2 |
| Phenoxyethanol | 0.162 |
| Wheat amino acids | 0.14 |
| Polyquaternium-39 | 0.1 |
| Alcohol denat. | 0.095 |
| Citric acid | 0.06 |
| Methyldibromo glutaronitrile | 0.04 |
| Tetrasodium EDTA | 0.02 |
| *Origanum vulgare* | 0.009 |
| *Panax ginseng* | 0.006 |
| *Morus alba* | 0.0046 |

EDTA, citric acid, benzophenone-4 and sodium chloride were added and mixed using a propeller stirrer until all materials were dissolved and uniform. The sodium laureth sulfate and piroctone olamine were then added and stirred until homogenous. The remaining materials, including the antioxidant complex were then added and the product was stirred until uniform and homogenous. The product was made to weight with purified water.

EXAMPLE 12

Deep Cleaning Shampoo

| Ingredients | % W/W |
| --- | --- |
| Aqua | to 100 |
| Sodium laureth sulfate | 14.13 |
| Sodium chloride | 2.72 |
| Cocamidopropyl betaine | 1.4 |
| PEG-6 cocamide | 1 |
| Parfum | 0.5 |
| Panthenol | 0.375 |
| Propylene glycol | 0.29 |
| Benzophenone-4 | 0.2 |
| Phenoxyethanol | 0.162 |
| Wheat amino acids | 0.14 |

-continued

| Ingredients | % W/W |
| --- | --- |
| Alcohol denat. | 0.095 |
| Methyldibromo glutaronitrile | 0.04 |
| Citric acid | 0.02 |
| Tetrasodium EDTA | 0.02 |
| *Origanum vulgare* | 0.009 |
| *Panax ginseng* | 0.006 |
| *Morus alba* | 0.0046 |

Citric acid, EDTA and sodium chloride were added to the water and dissolved. The benzophenone-4, sodium laureth sulfate, cocamidopropyl betaine, panthenol, methydibromo glutaronitrile, wheat amino acids and the antioxidant complex were then added and mixed until the product was uniform, using a propeller stirrer. The parfum was pre-dispersed in the PEG-6 cocamide and then added to the bulk. The product was made to weight using purified water.

EXAMPLE 13

Moisturising Shampoo

| Ingredients | % W/W |
| --- | --- |
| Aqua | to 100 |
| Sodium laureth sulfate | 8.24 |
| Cocamidopropyl betaine | 2.8 |
| Cocamide DEA | 1.63 |
| Panthenol | 1.5 |
| Sodium chloride | 1.5 |
| Laureth-3 | 1.194 |
| Parfum | 0.5 |
| Propylene glycol | 0.5 |
| Polyquaternium-10 | 0.273 |
| Glycerin | 0.2 |
| Wheat amino acids | 0.14 |
| Alcohol denat. | 0.095 |
| Dimethicone propyl PG-betaine | 0.09 |
| Citric acid | 0.04 |
| Tetrasodium EDTA | 0.02 |
| *Origanum vulgare* | 0.009 |
| *Panax ginseng* | 0.006 |
| *Morus alba* | 0.0046 |

EDTA and polyquaternium-10 were added to the water and the polymer was hydrated using an homogeniser. The citric acid, sodium chloride and benzophenone-4 were added and stirred until uniform. The remaining materials, including the antioxidant complex were added individually and the product was mixed using a propeller stirrer until homogenous. The product was made to weight using purified water.

EXAMPLE 14

Extra Hold Hair Gel

| Ingredients | % W/W |
| --- | --- |
| Aqua | to 100 |
| PVP/VA copolymer | 1.9 |
| Propylene glycol | 1.29 |
| Carbomer | 1 |
| PEG-40 hydrogenated castor oil | 1 |
| Panthenol | 0.375 |

-continued

| Ingredients | % W/W |
| --- | --- |
| Sodium hydroxide | 0.26 |
| Parfum | 0.2 |
| Phenoxyethanol | 0.16 |
| Tetrasodium EDTA | 0.15 |
| Mica | 0.113 |
| Cystine hydroxypropyl polysiloxane | 0.1 |
| Alcohol denat. | 0.095 |
| Methyldibromo glutaronitrile | 0.04 |
| Sodium chloride | 0.03 |
| Wheat amino acids | 0.028 |
| Benzophenone-2 | 0.025 |
| *Origanum vulgare* | 0.009 |
| *Panax ginseng* | 0.006 |
| *Morus alba* | 0.0046 |

Method

EDTA, methyldibromo glutaronitrile, PVP/VA copolymer and carbomer were added to the water and mixed using a homogeniser to ensure that the polymers were hydrated. With continued homogenising, the cystine hydroxypropyl polysiloxane was added and mixed into the product. The remaining materials, including the antioxidant complex were added individually and mixed using a propeller strirrer until the product was homogenous.

EXAMPLE 15

Gentle Shampoo

| Ingredients | % W/W |
| --- | --- |
| Aqua | to 100 |
| Sodium laureth sulfate | 8.25 |
| Cocamidopropyl betaine | 2.8 |
| Sodium chloride | 1.794 |
| Cocamide DEA | 1.63 |
| PEG-6 cocamide | 1 |
| Parfum | 0.5 |
| Panthenol | 0.375 |
| Propylene glycol | 0.29 |
| Benzophenone-4 | 0.2 |
| Glycerin | 0.2 |
| Phenoxyethanol | 0.162 |
| Wheat amino acids | 0.14 |
| Alcohol denat. | 0.095 |
| Citric acid | 0.05 |
| Methyldibromo glutaronitrile | 0.04 |
| Tetrasodium EDTA | 0.02 |
| *Origanum vulgare* | 0.2 |
| *Panax ginseng* | 0.2 |
| *Morus alba* | 0.2 |

EDTA, sodium chloride, citric acid and benzophenone-4 were added to the water. This was followed by the addition of sodium laureth sulfate, methyldibromo glutaronitrile, wheat amino acids and the antioxidant complex. PEG-6 cocamide and cocamide DEA were heated gently until liquified. The parfum was added and mixed. This was then added to the above mixture. The cocamidopropyl betaine and remaining materials were then added and mixed. The product was made to weight using purified water.

EXAMPLE 16

Gentle Shampoo

| Ingredients | % W/W |
|---|---|
| Aqua | to 100 |
| Sodium laureth sulfate | 8.25 |
| Cocamidopropyl betaine | 2.8 |
| Sodium chloride | 1.794 |
| Cocamide DEA | 1.63 |
| PEG-6 cocamide | 1 |
| Parfum | 0.5 |
| Panthenol | 0.375 |
| Propylene glycol | 0.29 |
| Benzophenone-4 | 0.2 |
| Glycerin | 0.2 |
| Phenoxyethanol | 0.162 |
| Wheat amino acids | 0.14 |
| Alcohol denat. | 0.095 |
| Citric acid | 0.05 |
| Methyldibromo glutaronitrile | 0.04 |
| Tetrasodium EDTA | 0.02 |
| *Origanum vulgare* | 0.2 |
| *Panax ginseng* | 0.2 |
| *Rosmarinus officinalis* | 0.2 |

EDTA, sodium chloride, citric acid and benzophenone-4 were added to the water. This was followed by the addition of sodium laureth sulfate, methyldibromo glutaronitrile, wheat amino acids and the antioxidant complex. PEG-6 cocamide and cocamide DEA were heated gently until liquified. The parfum was added and mixed. This was then added to the above mixture. The cocamidopropyl betaine and remaining materials were then added and mixed. The product was made to weight using purified water.

A number of trials were conducted to demonstrate the efficacy of the synergistic combinations of anti-free radical agents.

In Vitro Tests

Linoleic acid (model skin and hair lipid) was incubated in the presence of various antioxidants and antoxidant combinations and was exposed to broad spectrum UVA/B to induce oxidation of the lipid. Following extraction of the lipid into methanol, the amount of lipid hydroperoxides (free radical generated damage) formed were measured with a specific colorimetric biochemical test. The degree of inhibition afforded by the antioxidants was thus measured and compared to irradiated vehicle controls.

The percentage inhibition of free radical mediated lipid peroxidation when compared to the vehicle alone are given below.

| Antioxidants | % inhibition |
|---|---|
| *Morus alba* (ma) | 0 |
| *Origanum vulgare* (ov) | 49 |
| *Panax ginseng* (pg) | 5.7 |
| Sodium ascorbyl phosphate (nap) | 21 |
| Grape seed (gs) | 0 |
| *Camellia sinensis* (cc) | 19 |
| Observed effect of nap/pg/ov | 100 |
| Predicted effect of nap/pg/ov | 75.7 |
| Observed effect of nap/ma/ov | 100 |
| Predicted effect of nap/ma/ov | 70 |
| Observed effect of nap/ma/cc | 100 |
| Predicted effect of nap/ma/cc | 40 |
| Observed effect of nap/ma/gs | 81 |
| Predicted effect of nap/ma/gs | 21 |

Thus it can be seen that the observed inhibiting effect of using the above combinations of antioxidants is greater than that which would be expected from the sum of the contributions of the individual thus demonstrating a synergistic effect.

In a second series of experiments using antoxidants collected in a later season gave the following results.

| Antioxidant | % inhibition |
|---|---|
| *morus alba* (ma) | 37 |
| *origanum vulgare* (ov) | 29 |
| *rosmarinus officinalis* (ro) | 15 |
| *panax ginseng* (pg) | 10 |
| Observed effect of ro/pg/ov | 88 |
| Predicted effect of ro/pg/ov | 54 |
| Observed effect of pg/ma/ov | 93 |
| Predicted effect of pg/ma/ov | 76 |

Thus it can be seen that the observed inhibiting effect of using the above combinations of antioxidants is greater than that which would be expected from the sum of the contributions of the individual thus demonstrating a synergistic effect.

In Vivo Tests

Swatches of hair were bed at each end and then cut into two pieces. One of these pieces was used as a test and the other was used as a control. Each piece was washed with either the shampoo under test or a control containing no anti-free-radical agents for one minute and then rinsed in tepid water for 30 seconds. The swatches were then fixed on a plate and irradiated with broad spectrum UVA/B light for 8 hours in the Heredus Suntest plus to induce oxidation of the lipid. Samples of each swatch (0.12 g) were weighed out and placed in an epindorph tube. A 2:1 mixture of chloroform and methanol (1 m) was added. The tubes were placed in a centrifuge tube, placed on a tumbula mixer and mixed for 2 hours in a refrigerator. The hair was removed and the solvent removed under nitrogen. The lipids were resolubilised by adding methanol (50 $\mu$l) and vortexing for 15 seconds. Aliquots (7.5 $\mu$l) were plated out in triplicate and assayed for the level of oxidised lipid using a commercially available specific colourimetric biochemical test (K-Assay LPO kit). Each test was repeated with 5 separate hair swatches and the mean result for each of the 3 determinations for all five swatches enabled the amount of oxidised lipid to be measured.

The composition of Example 1 containing *morus alba* (0.2%), *origanum vulgare* (0.2%) and *panax ginseng* (0.2%) showed an amount of oxidised lipid of 113 nmol/ml compared to 181 nmol/ml for the control. The reduction in the amount of oxidised lipid is therefore around 38%.

The composition of Example 8 containing *morus alba* (0.2%), *origanum vulgare* (0.2%) and *panax ginseng* (0.2%) showed an amount of oxidised lipid of 372 nmol/ml compared to 553 nmol/ml for the control. The reduction in the amount of oxidised lipid is therefore around 33%.

The composition of Example 15 containing *morus alba* (0.2%), *origanum vulgare* (0.2%) and *panax ginseng* (0.2%) showed an amount of oxidised lipid of 482 nmol/ml compared to 731 nmol/ml for the control. The reduction in the amount of oxidised lipid was around 34%.

The composition of Example 16 containing *rosmarinus officinalis* (0.2%), *origanum vulgare* (0.2%) and *panax ginseng* (0.2%) showed an amount of oxidised lipid of 601 nmol/ml compared to 694 nmol/ml for the control. The reduction in the amount of oxidised lipid was around 13%.

Sensory Analysis

Swatches of hair treated with either base formulation or formulations containing antioxidants were assessed by an expert panel for factors such as shine. softness, static, ease of combing, gloss and overall feel. Statistical analysis was used to determine whether antioxidants were able to protect and enhance these properties.

The results showed an improvement in shine and feel.

What is claimed is:

1. Hair care composition comprising a synergistic mixture of three anti-free-radical agents selected from the group consisting of
   (a) sodium ascorbyl phosphate or magnesium ascorbyl phosphate
   (b) *morus alba;*
   (c) *origanum vulgare;*
   (d) *panax ginseng;*
   (e) *rosmarinus officinalis;*
   (f) *camellia sinenis;* and
   (g) grape seed extract;
in a suitable diluent or carrier.

2. The hair care composition of claim 1, wherein (A) is sodium ascorbyl phosphate.

3. The hair care composition of claim 1, wherein the total amount of anti-free radical agents present ranges from about 0.003 to about 10% by weight.

4. The hair composition of claim 1, wherein the total amount of anti-free-radical agents present ranges from 0.005 to about 1% by weight.

5. The hair care composition of claim 1, wherein the total amount of anti-free-radical agents present ranges from about 0.01 to about 0.6% by weight.

6. The hair care composition of claim 1 where the synergistic combination of anti-free radical agents is one combination selected from the group consisting of:

*Origanum vulgare*, sodium ascorbyl phosphate and *morus alba;*

*Origanum vulgare*, sodium ascorbyl phosphate and *panax ginseng;*

*Panax ginseng, morus alba* and *origanum vulgare;*

Sodium ascorbyl phosphate, *morus alba* and grape seed; and

*Origanum vulgare, panax ginseng* and *rosmarinus officinalis.*

7. A method of treating hair comprising applying to said hair the hair care composition of claim 1.

8. The composition of claim 1, wherein the total amount of anti-free-radical agents present in said composition is below the level that causes staining of skin or clothes or dyeing of hair.

9. The composition of claim 1, wherein said composition further comprises at least one sunscreen agent.

10. The composition of claim 1, wherein said composition further comprises at least one pH adjusting agent.

11. The composition of claim 1, wherein said composition further comprises at least one buffer system.

12. The composition of claim 1, wherein said composition further comprises at least one antidandruff agent.

13. The composition of claim 1, wherein said composition comprises *origanum vulgare*, sodium ascorbyl phosphate and *morus alba.*

14. The composition of claim 1, wherein said composition comprises *origanum vulgare*, sodium ascorbyl phosphate and *panax ginseng.*

15. The composition of claim 1, wherein said composition comprises *panax ginseng, morus alba* and *origanum vulgare.*

16. The composition of claim 1, wherein said composition comprises sodium ascorbyl phosphate, *morus alba* and grape seed.

17. The composition of claim 1, wherein said composition comprises *origanum vulgare, panax ginseng* and *rosmarinus officinalis.*

* * * * *